United States Patent [19]
Aebischer et al.

[11] Patent Number: 5,389,535
[45] Date of Patent: * Feb. 14, 1995

[54] METHOD OF ENCAPSULATING CELLS IN A TUBULAR EXTRUDATE

[75] Inventors: Patrick Aebischer, Barrington, R.I.; Lars Wahlberg, Gävle, Sweden

[73] Assignee: Brown University Research Foundation, Providence, R.I.

[*] Notice: The portion of the term of this patent subsequent to Oct. 27, 2009 has been disclaimed.

[21] Appl. No.: 169,169

[22] Filed: Dec. 17, 1993

Related U.S. Application Data

[63] Continuation of Ser. No. 827,728, Feb. 26, 1992, Pat. No. 5,284,761, which is a continuation of Ser. No. 461,999, Jan. 8, 1990, Pat. No. 5,158,881, which is a continuation-in-part of Ser. No. 121,626, Nov. 17, 1987, Pat. No. 4,892,538.

[51] Int. Cl.$^6$ .................. C12N 11/04; C12N 5/00; C12M 1/40; B01J 13/02
[52] U.S. Cl. .................. 435/182; 264/4; 264/4.7; 425/382 R; 435/179; 435/180; 435/240.22; 435/240.23; 435/288
[58] Field of Search ............. 435/179, 180, 182, 288, 435/240.22, 240.23; 264/4, 4.7; 425/382 R, 382.2

[56] References Cited

U.S. PATENT DOCUMENTS

| | | | |
|---|---|---|---|
| 3,093,831 | 6/1963 | Jordan | 3/1 |
| 3,715,277 | 2/1973 | Dinelli et al. | 195/63 |
| 3,821,087 | 6/1974 | Knazek et al. | 195/127 |
| 3,947,325 | 3/1974 | Dinelli et al. | 195/68 |
| 3,962,383 | 6/1976 | Hagimara et al. | 264/4 |
| 4,163,691 | 8/1979 | Deros et al. | 435/174 |
| 4,241,187 | 12/1980 | White | 435/284 |
| 4,251,195 | 2/1981 | Suzuki et al. | 425/6 |
| 4,288,494 | 9/1981 | Porter et al. | 428/398 |
| 4,324,683 | 4/1982 | Lim et al. | 252/316 |
| 4,333,906 | 1/1982 | Porter et al. | 264/40.3 |
| 4,352,883 | 10/1982 | Lim | 435/178 |
| 4,353,888 | 10/1982 | Sefton | 424/25 |
| 4,378,016 | 3/1983 | Loeb | 128/260 |
| 4,391,909 | 7/1983 | Lim | 435/178 |

(List continued on next page.)

FOREIGN PATENT DOCUMENTS

| | | |
|---|---|---|
| 116311 | 8/1984 | European Pat. Off. . |
| 147939 | 7/1985 | European Pat. Off. . |
| 161640 | 11/1985 | European Pat. Off. . |
| 188309 | 7/1986 | European Pat. Off. . |
| 363125 | 4/1990 | European Pat. Off. . |
| 2189809 | 11/1987 | United Kingdom . |
| 2192171 | 1/1988 | United Kingdom . |
| WO87/04367 | 7/1987 | WIPO . |

OTHER PUBLICATIONS

Seftan, et al., Biotechnology & Bioengineering, vol. XXIX, 1987, pp. 1135–1143.
Sugamori, et al., Trans. Am. Soc. Artif. Intern. Organs., vol. XXXV, 1985, pp. 791–799.
Schratter, "Cell Culture with Synthetic Capillaries," Meth. Cell Biology, 14, pp. 95–103 (1976).
Tze et al., "Implantable Artificial Endocrine Pancreas (List continued on next page.)

Primary Examiner—David M. Naff
Attorney, Agent, or Firm—Fish & Neave

[57] ABSTRACT

Methods and systems are disclosed for encapsulating viable cells which produce biologically-active factors. The cells are encapsulated within a semipermeable, polymeric membrane by co-extruding an aqueous cell suspension and a polymeric solution through a common port to form a tubular extrudate having a polymeric outer coating which encapsulates the cell suspension. For example, the cell suspension and the polymeric solution can be extruded through a common extrusion port having at least two concentric bores, such that the cell suspension is extruded through the inner bore and the polymeric solution is extruded through the outer bore. The polymeric solution coagulates to form an outer coating. As the outer coating is formed, the ends of the tubular extrudate can be sealed to form a cell capsule. In one embodiment, the tubular extrudate is sealed at intervals to define separate cell compartments connected by polymeric links.

20 Claims, 4 Drawing Sheets

U.S. PATENT DOCUMENTS

| | | | |
|---|---|---|---|
| 4,402,694 | 9/1983 | Ash et al. | 604/891 |
| 4,409,331 | 10/1983 | Lim | 435/178 |
| 4,426,337 | 1/1984 | Suzuki et al. | 264/4 |
| 4,451,253 | 5/1984 | Harman | 604/60 |
| 4,495,288 | 1/1985 | Jarris, Jr. et al. | 435/241 |
| 4,686,098 | 8/1987 | Kopchick et al. | 424/424 |
| 4,695,466 | 9/1987 | Morishita et al. | 424/456 |
| 4,892,538 | 1/1990 | Aebischer et al. | 604/891.1 |
| 4,902,295 | 2/1990 | Walthall et al. | 623/11 |
| 4,902,450 | 2/1990 | Morrison | 264/4 |
| 5,158,881 | 1/1992 | Aebischer et al. | 435/182 |
| 5,284,761 | 2/1994 | Aebischer et al. | 435/182 |

OTHER PUBLICATIONS

Unit Used To Restore Normoglycaemia In The Diabetic Rat," *Nature*, 264, pp. 466–467 (1976).

Chang, "Encapsulation of Enzymes, Cell Contents, Cells, Vaccines, Antigens, Antiserum, Cofactors, Hormones, and Proteins," *Biomeical Applications of Immobilized Enzymes and Protein*, 1, pp. 69–90 (1977).

Sun et al., "The Use, in Diabetic Rates and Monkeys, of Artifical Capillary Units Containing Cultured Islets of Langehans (Artificial Endocrine Pancreas)," *Diabetes*, 26, pp. 1136–1139 (1977).

"Apparatus for Manufacturing Capsules Containing Microorganisms has Reverse Cone Rotating Containers," Patent Abstract JP 62100288 (May 9, 1987).

"Production Apparatus For Microorganism-Containing Capsule," *Patent Abstracts of Japan*, 11, No. 315 (Oct. 14, 1987).

Aebischer et al., "Transplantation Of Neural Tissue In Polymer Capsules," *Brain Research*, 448, pp. 364–368 (1988).

Winn et al., "An Encapsulated Dopamine-Releasing Polymer Alleviates Experimental Parkinsonism in Rats," *Experimental Neurology*, 105, pp. 244–250 (1989).

Winn et al., "Brain Tissue Reaction to Permselective Polymer Capsules," *J. Biomed. Mater. Res.*, 23, pp. 31–44 (1989).

Hoffman et al., "NGF Released From a Polymer Matrix Prevents Loss of ChAT Expression in Basal Forebrain Neurons Following a Fimbria-Fornix Lesion," *Experimental Neurology*, 110, pp. 39–44 (1990).

Jaeger et al., "Polymer Encapsulated Dopaminergic Cell Lines as 'Alternative Neural Grafts,'" *Progress In Brain Research*, 82, pp. 41–46 (1990).

Aebischer et al., "Treating Parkinson's Disease With Lesions of the Subthalamic Nucleus," *Science*, 252, p. 133 (1991).

Aebischer et al., "Transplantation of Microencapsulated Bovine Chromaffin Cells Reduces Lesion-Induced Rotational Asymmetry in Rats," *Brain Research*, 560, pp. 43–49 (1991).

Aebischer et al., "Transplantation of Polymer Encapsulated Neurotransmitter Secreting Cells: Effect of the Encapsulation Technique," *J. Biomec. Engineering*, 113, pp. 178–183 (1991).

Aebischer et al., "Long-Term Cross-Species Brain Transplantation of a Polymer-Encapsulated Dopamine-Secreting Cell Line," *Experimental Neurology*, 111, pp. 269–275 (1991).

Aebischer et al., "Macroencapsulation of Dopamine-Secreting Cells by Coextrusion With an Organic Polymer Solution," *Biomaterials*, 12, pp. 50–56 (1991).

Jaeger et al., "Repair of the Blood-Brain Barrier Following Implantation of Polymer Capsules," *Brain Research*, 551, pp. 163–170 (1991).

Winn et al., "Behavioral Recovery Following Intrastriatal Implantation of Microencapsulated PC12 Cells," *Experimental Neurology*, 113, pp. 322–329 (1991).

Tresco et al., "Polymer Encapsulated Neurotransmitter Secreting Cells—Potential Treatment for Parkinson's Disease," *Asaio Journal*, 38, pp. 17–23 (1992).

METHOD OF ENCAPSULATING CELLS IN A TUBULAR EXTRUDATE

REFERENCE TO RELATED APPLICATIONS

This application is a continuation of application Ser. No. 07/827,728, filed Feb. 26, 1992, now U.S. Pat. No. 5,284,761, which is a continuation of application Ser. No. 07/461,999, filed Jan. 8, 1990, now U.S. Pat. No. 5,158,881, which is a continuation-in-part of application Ser. No. 07/121,626, filed Nov. 17, 1987, U.S. Pat. No. 4,892,538.

BACKGROUND OF THE INVENTION

The technical field of this invention concerns methods and systems for encapsulating living cells for the production of biologically active factors.

There is considerable interest at present in the biologically active products of living cells, including, for example, neurotransmitters, hormones, cytokines, nerve growth factors, anglogenesis factors, blood coagulation factors, lymphokines, enzymes and other therapeutic agents. There is also substantial interest in developing new methods and systems for producing such biological factors as well as in delivering these factors to subjects for therapeutic purposes.

For example, Parkinson's disease is characterized by the degeneration of the dopaminergic nigrostriatal system. Striatal implantation of polymer rods which release sustained amounts of a neurotransmitter, dopamine, has been reported to alleviate experimental Parkinsonism in rodents, indicating that the release of dopamine alone in the proper target structure may be able to correct this functional deficiency.

In contrast to the limited capacity of a polymeric matrix drug release system, encapsulated dopamine-releasing cells have been proposed as a means to provide a continuous supply of neurotransmitters. The encapsulation of neurotransmitter-secreting cells by a permselective membrane which permits diffusion of the biological factor may not only prohibit the escape of mitotically active cells, but also prevent host rejection in the case of cross-species transplantation.

A number of researchers have proposed the use of microcapsules—tiny spheres which encapsulate a microscopic droplet of a cell solution—for both therapeutic implantation purposes and large scale production of biological products. However, there are a number of shortcomings to the microencapsulation approach: the microcapsules can be extremely difficult to handle (and retrieve, after implantation); their volume is limited; and the types of encapsulating materials which can be used are constrained (by the formation process) to polymers which can dissolve in biocompatible solvents.

An alternative approach has been macroencapsulation, which typically involves loading cells into hollow fibers and then closing the extremities at both ends with a polymer glue. In contrast to microcapsules, macrocapsules offer the advantage of easy retrievability, an important feature in therapeutic (especially, neural) implants. However, the construction of macrocapsules in the past has often been tedious and labor intensive. Moreover, due to unreliable closure, conventional methods of macroencapsulation have provided inconsistent results.

There exists a need for better techniques for macroencapsulation of cells for both therapeutic implantation and industrial production purposes. Encapsulation techniques which can be practiced in a an automated fashion, and which permit the usage of a wider range of materials and/or provide more reliable closure would satisfy a long felt need in the art.

SUMMARY OF THE INVENTION

Methods and systems are disclosed for encapsulating viable cells which produce biologically-active factors. The cells are encapsulated within a semipermeable, polymeric membrane by co-extruding an aqueous cell suspension and a polymeric solution through a common port to form a tubular extrudate having a polymeric outer coating which encapsulates the cell suspension.

In one aspect of the invention, methods are disclosed in which the cell suspension and the polymeric solution are extruded through a common extrusion port having at least two concentric bores, such that the cell suspension is extruded through the inner bore and the polymeric solution is extruded through the outer bore. The polymeric solution coagulates to form an outer coating. As the outer coating is formed, the ends of the tubular extrudate can be sealed to form a cell capsule. In one illustrated embodiment, the tubular extrudate is sealed at intervals to define separate cell compartments connected by polymeric links.

Strings of cell capsules formed in this manner have a number of advantages over conventional, cell-encapsulating products. The multi-compartment form ensures that breaks in the tubular membrane can be contained to individual cell capsules. Moreover, the design is particularly advantageous in preparing implantable cell cultures for delivery of biologically-active factors to a subject for therapeutic purposes. The string of cell capsules can be coiled, twisted or otherwise deposited in various shapes to provide a dense and compact structure for implantation. Because the cell capsules are connected to each other, they can also be readily retrieved, if necessary, following implantation. The string-like nature of these products is particularly preferable over individual spherical microcapsules which typically are retrieved by aspiration (often resulting in a high percentage of unretrievable capsules and, consequently, inflamation in the subject).

Multi-compartment cell capsule strings can be formed from the tubular extrudate of the present invention by sealing the extrudate at intervals using various techniques. For example, the extrudate can be sealed by compressing it at intervals using mechanical or pneumatic force. Alternatively, the pressure under which the cell suspension or the polymeric solution is extruded can be modified to collapse the tubular extrudate at intervals and define separate cell compartments. In yet another technique, the flow of the cell suspension can be interrupted or otherwise impeded at intervals to likewise collapse the tubular extrudate and define cell compartments.

The products of the present invention are particularly well-suited for use and therapeutic implant devices, such as those disclosed in co-pending U.S. patent application Ser. No. 121,626, "In Vivo Delivery Of Neurotransmitters By Implanted, Encapsulated Cells" by Aebischer et al. filed Nov. 17, 1987, herein incorporated by reference. In U.S. patent application Ser. No. 121,626, techniques are disclosed for implanting encapsulated neurotransmitter-secreting cells into a target region within a subject's brain, such that the encapsulated cells secret a neurotransmitter and thereby permit constitutive delivery of a therapeutic agent to treat a neurological deficiency, such as Parkinson's disease. Alternatively, artificial organs capable of secreting other biological factors, such as hormones (e.g., insulin, thymic factors and the like) can also be constructed using the tubular extrudates and multi-compartment cell capsule strings of the present invention.

The products of the present invention are also well-suited for use in bioreactors and other in virto culturing systems, for the production of drugs and other useful biological materials. In such applications, cells which produce such materials, either naturally, by mutation or by recombinant design, are encapsuled and allowed to synthesize the materials which are then collected following secretion into a circulating culture medium. Alternatively, the biological materials can be accumulated within the cell capsules (e.g., by appropriate control of the porosity) and then harvested the materials by removing the strands from the culture medium, lyzing the polymeric membranes and recovering the synthesized materials in concentrated form.

The polymeric coating is preferably a semipermeable membrane, that is to say, a porous structure capable of protecting transplanted cells from autoimmune or vital assault, as well as other detrimental agents in the external environment, while allowing essential nutrients, cellular waste products and cell secretions to diffuse therethrough. As used herein, the term "selectively permeable" or "semipermeable" is used to describe biocompatible membranes which allow diffusion therethrough of solutes having a molecular weight up to about 150,000 (Mr).

The permeability of the polymeric coating can be varied by controlling the viscosity of the polymeric solution, such that upon coagulation, the coating will form with a network of microchannels to provide diffusion pathways. In one embodiment, this can be achieved by employing a water-miscible solvent as a component of the polymeric solution and maintaining a pressure differential between the aqueous cell suspension and the polymeric solution during extrusion. As the tubular extrudate forms, water from the aqueous cell suspension infiltrates into the coagulating polymer to replace the solvent as the solvent is driven outward by the pressure difference. Upon coagulation, the water which has infiltrated into the polymeric coating provides a network of pores. The optimal pressure and viscosity will, of course, vary with the solvent and polymer employed but can be readily ascertained for any particular polymer/solvent combination by those skilled in the art without undue experimentation.

Various polymers can be used to form the membrane coatings of the present invention, including polymers derived from solutions which would otherwise be incompatible with the propagation of living cells. Because of the unique extrusion process disclosed in the present invention, solvents which would otherwise be toxic are quickly driven away from the aqueous cell suspension during the membrane formation process, thereby permitting the use of many new and potentially useful polymeric materials. For example, polymeric membranes can be formed from polyacrylates (including acrylic copolymers), polyvinylidienes, polyurethanes, polystyrenes, polyamides, cellulose acetates, cellulose nitrates, polysulfones, polyacrylonitriles, as well as derivatives, copolymers, and mixtures thereof.

The solvent for the polymer solution will depend upon the particular polymer chosen for the membrane material. Suitable solvents include a wide variety of organic solvents, such as alcohols and ketones, generally, as well as dimethylsulfoxide (DMSO), dimethyacetamide (DMA) and dimethylformimide (DMF), in particular. In general, water-miscible organic solvents are preferred.

The polymeric solution or "dope" can also include various additives, including surfactants to enhance the formation of porous channels, as well as antioxidants to sequester oxides that are formed during the coagulation process. Moreover, when the cell capsules of the present invention are designed for implantation, materials, such as anti-inflammatory agents and cell growth factors, can also be incorporated into the polymeric membrane to reduce immune response or stimulate the cell culture, respectively. Alternatively, these materials can be added to the multi-compartment cell capsule strands after formation by a post-coating or spraying process. For example, the strands can be immersed in a solution which contains an anti-inflammatory agent, such as a corticoid, an angiogenic factor, or a growth factor following extrusion to post-coat the cell capsules.

Various techniques can also be employed to control the smoothness or roughness of the outer surface of the polymeric coating. In some instances, a very smooth outer coating can be preferable to reduce scar tissue attachment and other immunoreactions during implantation. Such a smooth coating can be obtained by simultaneously immersing the tubular extrudate in a quenchent, such as a bath of physiological saline, or by applying a flowing, quenchent fluid during the extrusion (e.g., from a third, concentric, outermost bore in an extrusion head assembly). Alternatively, in some applications a rough outer surface with larger pores may be desired, for example, in instances where capillary ingrowth during implantation is desired, and such a rougher outer surface can be obtained by coagulation in air.

Various cell lines can be encapsulated according to the present invention. As noted above, the multi-compartment cell culture strings are particularly useful for the constitutive delivery of neurotransmitters, such as dopamine, which is secreted by cells of the adrenal medulla, embryonic ventral mesencephalic tissue and neuroblastic cell lines. PC12 cells (an immortalized cell line derived from a rat pheocromocytoma) are particularly preferred in some applications because of their ability to secrete large amounts of dopamine over long periods of time. Other neurotransmitters include gamma aminobutyric acid (GABA), serotonin, acetylcholine, noradrenaline and other compounds necessary for normal nerve functions. A number of cell lines are known or can be isolated which secrete these neurotransmitters. Cells can also be employed which synthesize and secrete agonists, analogs, derivatives or fragments of neurotransmitters which are active, including, for example, cells which secrete bromocriptine, a dopamine agonist, and cells which secrete L-dopa, a dopamine precursor.

In other embodiments of the invention, the encapsulated cells can be chosen for their secretion of hormones, cytokines, nerve growth factors, anglogenesis factors, antibodies, blood coagulation factors, lymphokines, enzymes, and other therapeutic agents.

The aqueous cell suspensions can further include various additives to protect the cells during the extrusion process or to stimulate their growth subsequently. Such additives can include, for example a nutrient medium or growth factors which are incorporated into the aqueous suspension, as well as an anchorage substrate material to enhance cell attachment. The anchorage substrate material can be a proteinaceous material, such as collagen, laminin, or polyamino acids. Alternatively, the cell suspension or the polymeric solution (or both) can include a foaming agent or a blowing agent which can distort the inner surface of the polymeric coating to increase the anchorage surface area of the tubular interior.

The products of the present invention can take various forms, including simple tubular extrudates as well as multi-compartment cell capsule strings. The shape of the multi-compartment strings can be tubular, resembling sausages, or nearly spherical, resembling strings of pearls. The maximum outer diameter of the strand with typically range from about 0.1 to about 1.0 millimeters. The membrane wall thickness will typically range from about 10 to about 100 microns. The length of the strands can be varied depending upon the particular application.

In another aspect of the invention, systems are disclosed for encapsulating cells to produce the tubular extrudate and multi-compartment cell capsule products described above. This system can include an extrusion head assembly (e.g., a spinneret or the like) having a first inner bore and a second, concentric, outer bore, as well as a cell suspension supply means for supplying the aqueous cell suspension to the inner bore of the extrusion head assembly, and a polymeric solution supply means for supplying the polymeric solution to the outer pore of the extrusion head assembly. As the cell suspension and polymeric solution are co-extruded, they form a tubular extrudate having a polymeric outer coating which encapsulate the cell suspension.

The tubular extrudate can be sealed at intervals by any one of a number of mechanisms. In one illustrated embodiment, two wheels with occluding elements on their periphery cooperate in rotation to periodically pinch the tubular extrudate and thereby seal it. This mechanical compression system can be replaced by a variety of other mechanical or pneumatic compression systems to seal the tubular extrudate at intervals.

Alternatively, the system can include a flow control means for varying the pressure differential between the aqueous cell suspension and the polymeric solution during co-extrusion. For example, each of the components supply means can include an infusion pump which is operated by a computer or other control element. In the normal operation, the infusion pumps are controlled to maintain a pressure differential between the aqueous cell suspension and the polymeric solution, such that the polymer solvent is driven outward during coagulation. By periodically varying the pressure, the tubular extrudate can be collapsed at intervals to define individual cell compartments. This can be accomplished, for example, by reducing the aqueous solution pressure. In some instances, it may be preferable to terminate the flow of the aqueous solution entirely and create a vacuum to ensure a complete seal between compartments.

Various other techniques can likewise be employed to interrupt the flow of the aqueous solution at intervals and thereby cause the tubular extrudate to collapse and form multiple compartments. For example, a retraction mechanism can be incorporated into the extrusion head assembly for moving the inner bore relative to the outer bore, such that the flow of the aqueous solution is interrupted to define separate cell compartments at intervals.

The systems disclosed herein can further include a quenchent bath for coagulating the polymeric solution following extrusion, and various mechanisms for drying the tubular extrudate as it emerges from the extrusion head, including blowers, or evacuation chambers. The extrusion head assembly can incorporate additional bores to provide multiple coatings or to deliver a quenchent fluid about the tubular extrudate. The system can also include a sedimentation chamber for the cell suspension, or an equivalent cell packing mechanism, to increase the cell density within the aqueous cell suspension.

The invention will next be described in connection with certain illustrated embodiments; however, it should be clear that various additions, subtractions or modifications can be made by those skilled in the art without departing from the spirit or scope of the invention.

DETAILED DESCRIPTION

Figure 1:
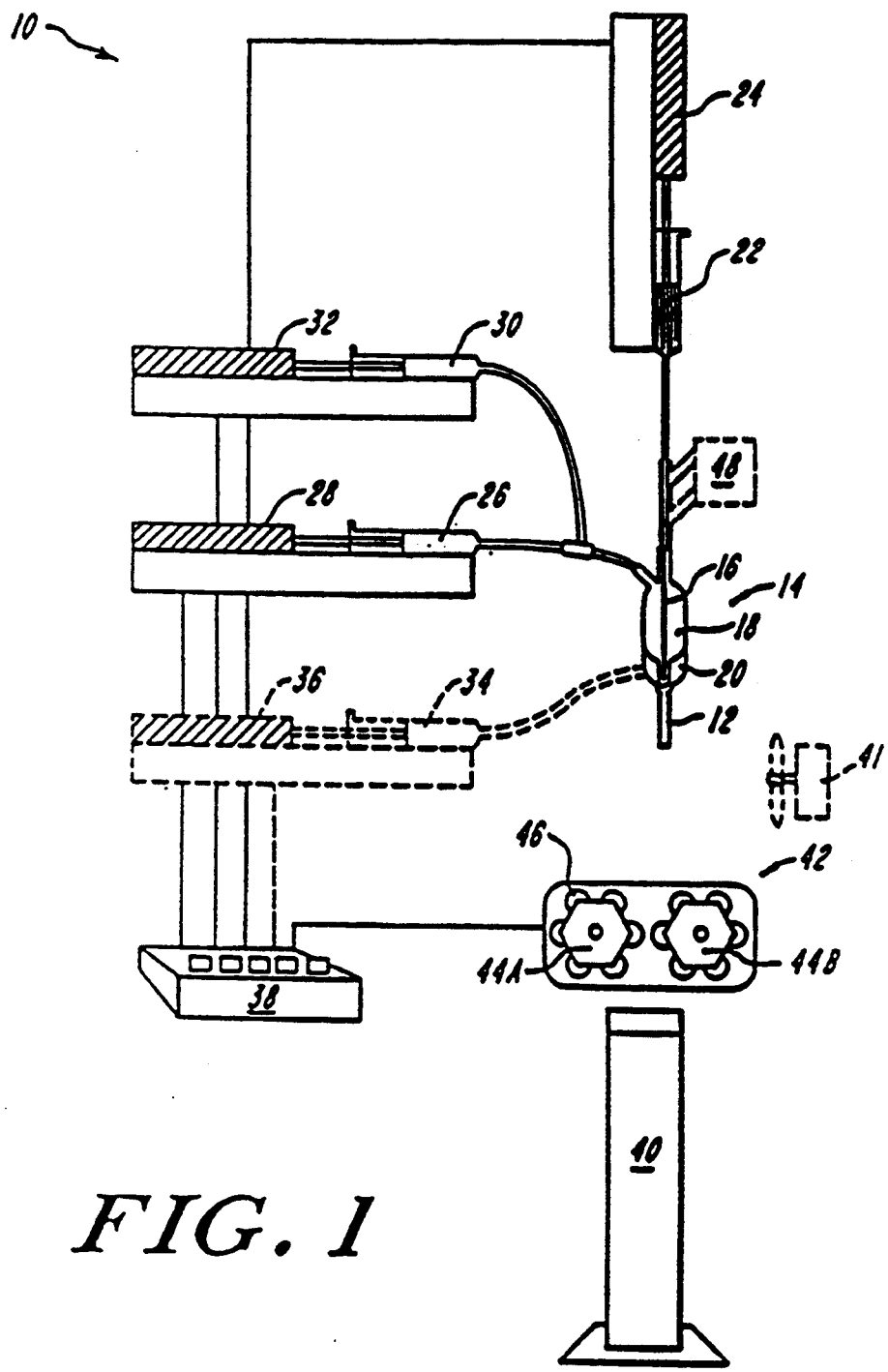
FIG. 1 is an overall schematic diagram of a system for encapsulating viable cells according to the invention.

In FIG. 1, a system 10 is shown for producing a tubular extrudate 12 according to the present invention, including an extrusion head 14 having a first (innermost) bore 16, a second outer bore 18 and, optionally, a third (outermost) bore 20. The system 10 further includes a cell suspension supply 22 and an associated pump 24, a polymer solution supply 26 and an associated pump 28 and, optionally, a flush solution supply 30 with a pump 32. Additionally, the system can also, optionally, include a outer flowing quenchent supply 34 with an associated pump 36. All of the pump elements can be controlled manually or, preferably, by an automated controller (e.g., a microprocessor) 38. The system 10 can also include a quenchent bath 40, which would normally be disposed directly below the extrusion head 14 during operation.

When the system 10 is employed to shape the tubular extrudate into a multi-compartment cell capsule string, a sealing means can be employed. One such sealing element 42 is shown in FIG. 1, including two motorized wheels 44A and 44B which have a series of protuberances 46 which cooperate during rotation to periodically pinch and seal the tubular extrudate as it passes between the wheels 44A and 44B.

Alternatively, a retraction means 48 can be employed to periodically retract the inner bore so as to interrupt the flow of the cell suspension. The effect of these retractions is to periodically seal the tubular extrudate and again form multiple compartments. In yet another alternative approach, the controller 38 can vary the pressure applied by pump 24 (and/or pump 28) to create periodic interruptions in the flow of the cell suspension.

Figure 2:
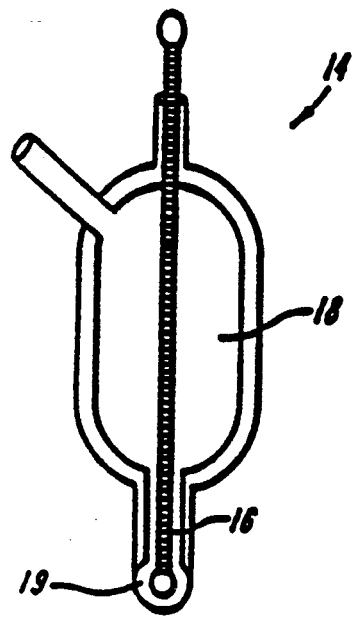
FIG. 2 is a more detailed schematic diagram of an extrusion head assembly for use in the system of FIG. 1.

In FIG. 2, the extrusion head 14 is shown in more detail, including an inner bore 16 for delivery of a cell suspension and an outer bore 18 for delivery of a polymeric solution. As the cell suspension and the polymeric solution are extruded through the common extrusion port 19, the polymeric solution coagulates to form an outer coating about the cell suspension.

Figure 3:
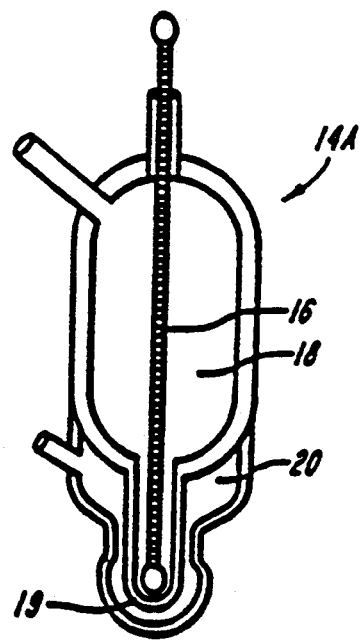
FIG. 3 is a schematic diagram of an alternative extrusion head assembly for use in the system of FIG. 1.

In FIG. 3, an alternative extrusion head 14A is shown in more detail comprising an inner bore 16 for the delivery of the cell suspension, a second bore 18 (surrounding the inner bore) for delivery of the polymeric solution, and an outer most bore 20 for delivery of a flowing quenchent fluid, such as saline. In this embodiment, a smooth coating can be obtained by simultaneously extruding the cell suspension and polymeric solution through common port 19 while applying a flowing quenchent fluid during the extrusion (e.g., from the outer most bore 20 in the extrusion head assembly 14A.)

Figure 4:
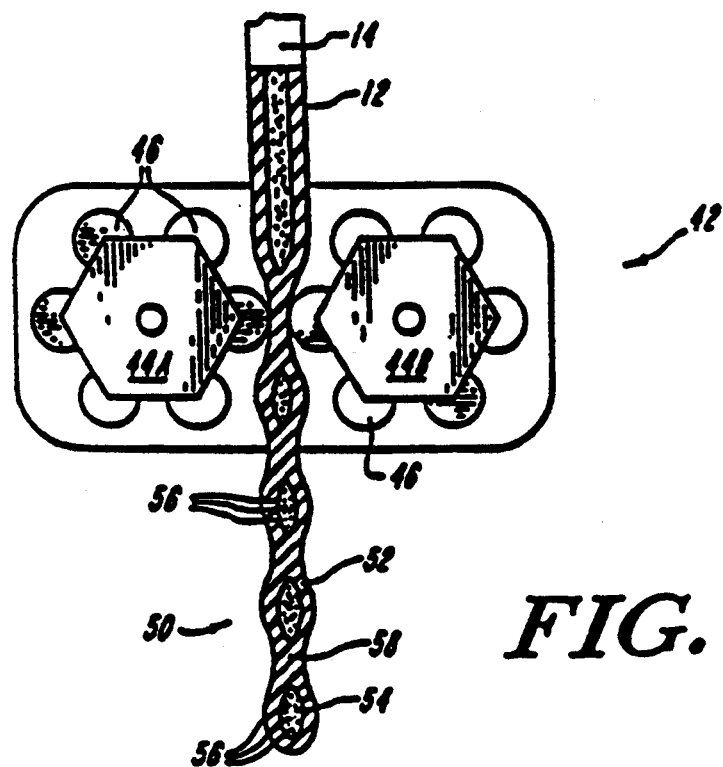
FIG. 4 is a schematic diagram of a mechanism for periodically sealing a tubular extrudate according to the invention to form a multi-compartment cell culturing vehicle.

In FIG. 4, the sealing element 42 of FIG. 1 is shown in more detail. Motorized wheels 44A and 44B are mounted on opposite sides of the tubular extrudate 12, such that upon rotation protuberances 46 on the wheels periodically come in contact with the extrudate 12 to pinch and seal the extrudate 12 as it exits the extrusion head 14. The wheels 44A and 44B can be mechanically linked and operated by a conventional motor under the control of a controller, such as shown in FIG. 1. The result of the periodic sealing of the extrudate 12 is a multi-compartment macrocapsule strand 50 having a polymeric membrane 52 surrounding an encapsulated cell solution 54 with individual cells 56 disposed therein. The individual cell capsules are joined to each another by connective filaments 58 where the protuberances 46 of the sealing means 42 has pinched the extrudate 12.

The invention will next be described in connection with certain illustrative, non-limiting

EXAMPLES

An extrusion system similar that illustrated in FIG. 1 was used, consisting of three electronically controlled programmable infusion pumps, a jet spinneret, two motor-controlled, coaxial wheel systems on the perimeter of which occluding polytetrafluoroethylene tubes were mounted, and an uptake system.

The macrocapsules were formed by injection of a polymeric solution into the outer tube of the spinneret. A coagulant, typically the encapsulated cells in their culture medium, was simultaneously injected in the spinneret inner tube. The encapsulating membrane was formed by a dry-jet, wet spinning process, i.e., the fast stabilization of the polymer solution emerging from the spinneret nozzle by the internal quench medium coupled with further stabilization in a quench bath. The closure of the fiber was performed by mechanically squeezing the forming hollow fiber with the coaxial wheel system prior to immersion in the quench bath. Near the spinneret head, the solvent concentration was sufficiently high to allow proper fusion of the fiber wall. Following each round of encapsulation, pure solvent was flushed automatically through the lumen of the spinneret to avoid clogging of the nozzle.

PC12 cells, an immortalized cell line derived from a rat pheocromocytoma which secretes large amounts of dopamine, were cultivated on collagen-coated tissue culture dishes in RPMI 1640 medium supplemented with 10% heat inactivated horse serum and 5% fetal calf serum. Dissociated bovine adrenal medullary cells, a non-dividing cell type which secretes dopamine, were maintained in DMEM medium supplemented with 5% fetal calf serum. Prior to encapsulation, the cells were harvested and loaded at a concentration of $1 \times 10^5$ cells/ml in a 3 ml syringe. A 15 percent vinylchloride-acrylonitrile copolymer solution in either dimethylsulfoxide (DMSO), dimethylformimide (DMF), or dimethylacetamide (DMAC) was loaded into a 5 ml glass syringe. Both solutions were then coextruded through the spinneret, and the capsules were collected in a physiologic saline solution. The capsules were rinsed and placed in individual wells containing the appropriate culture media.

Basal and potassium-evoked release of catecholamines was quantified under static incubation conditions by ion-pair reverse-phase high performance liquid chromatography (HPLC) equipped with electrochemical detection at 2 and 4 weeks. Morphological analysis, including light, scanning, and transmission electron microscopy, was performed on representative samples for each time period.

Figure 5:
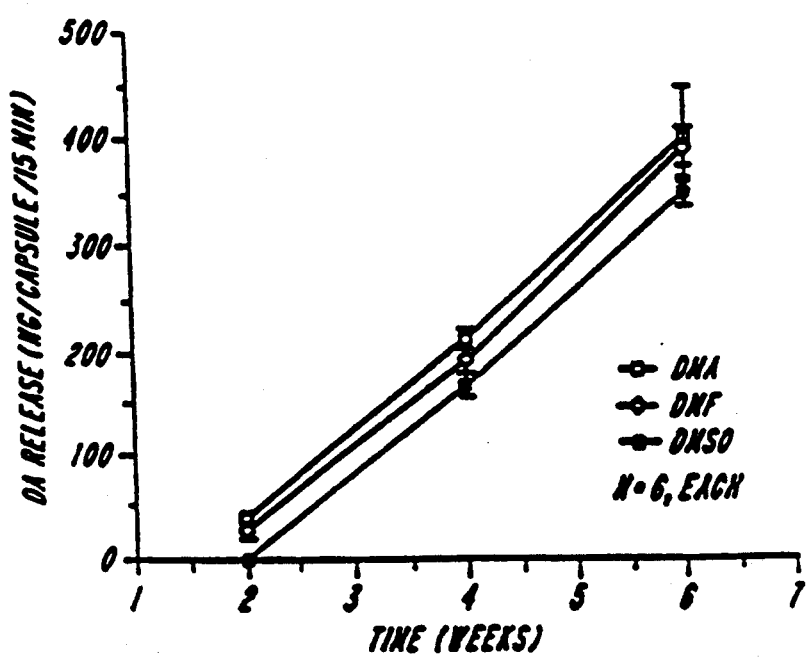
FIG. 5 is a graph showing dopamine release versus time for capsules containing dopamine secreting cells produced according to the present invention with three different solvent systems.

All cell-loaded capsules released dopamine into the medium under basal conditions at all time periods. High potassium treatment increased dopamine release from both PC12 and adrenal medullary cells. Dopamine output by PC12 cells, but not adrenal medullary cells, increased with time. The increase in dopamine release by the PC12 cell-loaded capsules over time is believed to be related to cell proliferation within the polymer capsule. No significant difference in dopamine release could be observed from PC12-loaded capsules extruded with the three different solvent systems (DMSO, DMF, DMAC), which suggests that the encapsulation technique of the present invention may prevent cell damage inflicted by solvents (FIG. 5). Due to the higher pressure of the inner bore system, the solvent was quickly driven toward the outside of the polymer capsule which prevented extended cell-solvent contact.

Morphological analysis revealed the presence of small clusters of PC12 cells randomly dispersed throughout the lumen of the capsule. At the electron microscope level, well-preserved PC12 cells, with their typical electron-dense secretory granules, could be observed. Cell division within the capsule space was suggested by the presence of numerous mitotic figures. Although initially coextruded as a cell suspension, adrenal chromaffin cells formed packed aggregates one week after encapsulation.

Figure 6:
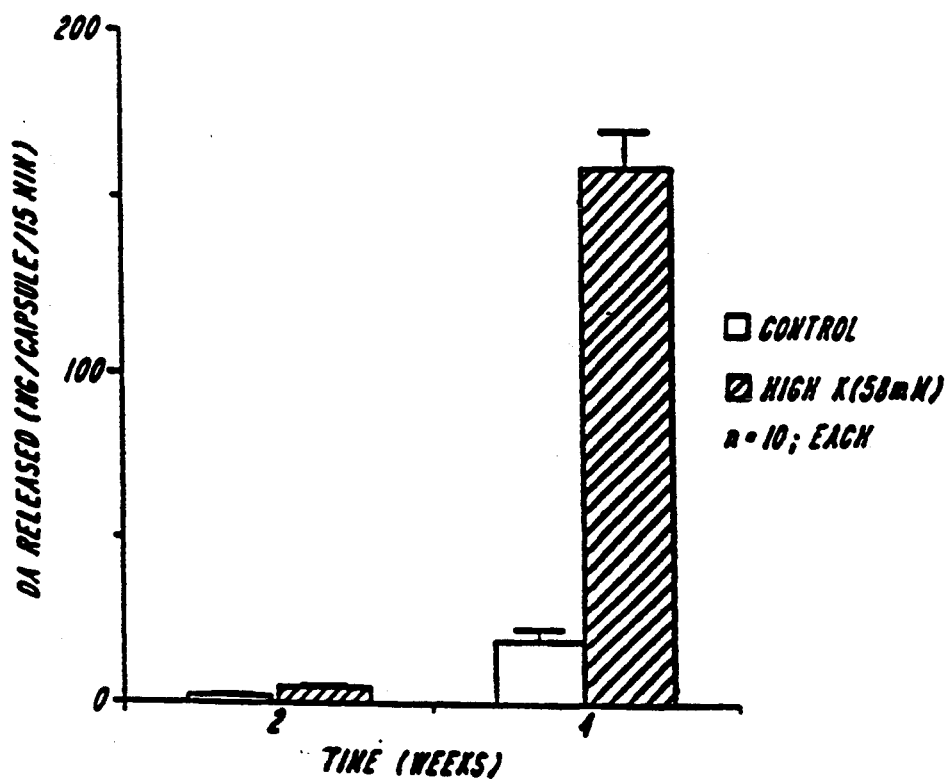
FIG. 6 is graph showing dopamine release by PC12 cells under normal and potassium-stimulated conditions at various times following encapsulation according to the invention.

FIG. 6 shows the results of an in vitro assay in which PC12 cells were encapsulated according to the present invention and monitored for release dopamine at two and four weeks following encapsulation. Dopamine levels were measured under both normal (controlled) conditions and also under a high potassium stimulation, which is known to induce depolarization of the cells and, consequently, to increase the secretion of dopamine in viable cells. As can be seen from the graph, there was little activity at two weeks; however, at four weeks the encapsulated cells exhibited dopamine secretions not only under normal conditions but also exhibited a strong response to the potassium stimulation, indicating that the cells were indeed viable in their encapsulated state.

Figure 7A:
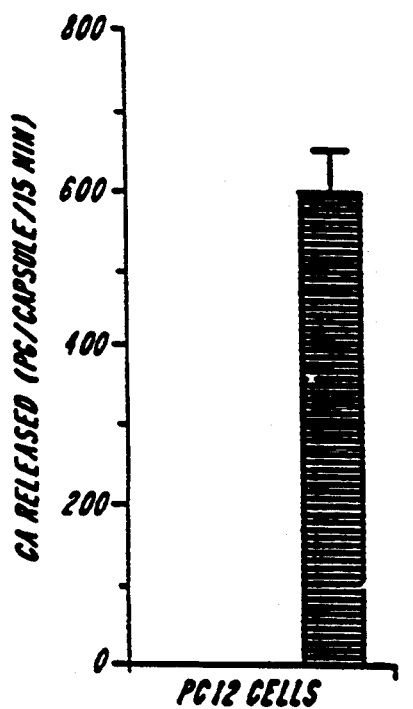
FIGS. 7A and 7B are graphs showing the release of catecholamines for PC12 cells and chromaffin cells respectively.
Figure 7B:
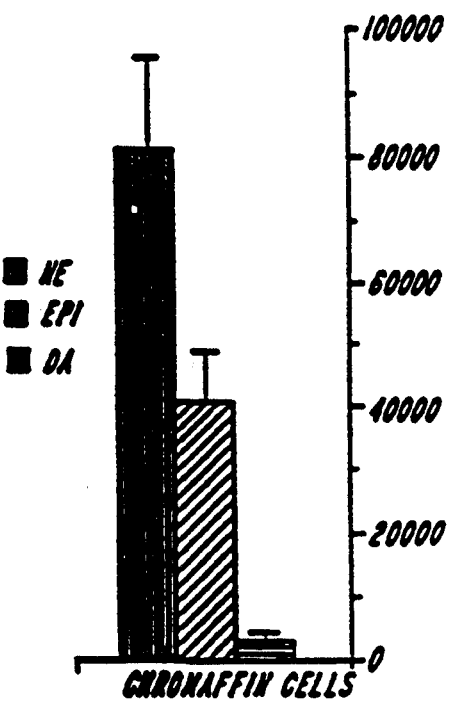

FIG. 7A and 7B show the result of another in vitro assay in which the secretions of both PC12 cells and chromaffin cells were monitored four weeks after encapsulation according to the present invention. Again, the cells were stimulated by high potassium concentrations and the medium while the PC12 cells released only dopamine, the chromaffin cells released a variety of catecholamines. The graft shows the levels of noradrenaline, epinephrine, and dopamine.

Due to their fluid dynamics, the macrocapsules extruded in accordance will the present invention should allow the use of a wider range of polymer/solvent systems and can constitute a more efficient encapsulation technique. The results show that immortalized and differentiated dopamine-secreting cells will survive in macroencapsulation. The ability of these capsules to spontaneously release dopamine over time suggests that polymer encapsulation can provide an alternative to the transplantation of non-encapsulated or microencapsulated dopamine-secreting cells in the treatment of Parkinson's disease.

We claim:

1. A method of encapsulating viable cells comprising co-extruding an aqueous cell suspension and a polymeric solution through a common port having at least two concentric bores to form a tubular extrudate having a polymeric outer coating which encapsulates said cell suspension, wherein said cell suspension is extruded through an inner bore and said polymeric solution is extruded through an outer bore and a pressure differential is maintained between said cell suspension and said polymeric solution during co-extrusion to impede solvent diffusion from said polymeric solution into said cell suspension, and said polymeric solution and said cell suspension are chosen so that coagulation of said polymeric solution occurs as the polymeric solution and cell suspension are extruded through the extrusion port.

2. The method of claim 1 wherein the extrusion port is in contact with air.

3. The method of claim 1 wherein the extrusion port is in contact with quenchent.

4. The method of claim 1 wherein said cell suspension comprises cells that secrete a biologically-active factor.

5. The method of claim 1 wherein said cell suspension comprises cells that secrete a neurotransmitter.

6. The method of claim 1 wherein said cell suspension further comprises a nutrient medium.

7. The method of claim 1 wherein said cell suspension further comprises an anchorage substrate material.

8. The method of claim 1 wherein said polymeric solution further comprises a water-miscible solvent component.

9. The method of claim 1 wherein said polymeric solution further comprises a surfactant.

10. The method of claim 1 wherein said polymeric solution further comprises an anti-inflammatory agent.

11. The method of claim 1 wherein said polymeric solution further comprises an antioxidant.

12. The method of claim 1 wherein the method further comprises controlling the viscosity of said polymeric solution, such that upon coagulation said outer polymeric coating will form a semipermeable membrane about said cell suspension.

13. A tubular extrudate comprising a semipermeable, polymeric membrane encapsulating a viable cell culture prepared by the method of claim 1.

14. The tubular extrudate of claim 13 wherein the membrane is permeable to molecules having a molecular weight of about 150,000 or less.

15. The tubular extrudate of claim 13 wherein the maximum outer diameter of the tubular extrudate ranges from abut 0.1 to about 1.0 millimeters.

16. The tubular extrudate of claim 13 wherein the membrane has a wall thickness ranging from abut 10 to about 100 microns.

17. The tubular extrudate of claim 13 wherein the polymeric membrane further comprises a polyacrylate material.

18. The tubular extrudate of claim 13 wherein the polymeric membrane further comprises a surfactant.

19. The tubular extrudate of claim 20 wherein the polymeric membrane further comprises an anti-inflammatory agent.

20. The tubular extrudate of claim 13 wherein the polymeric membrane further comprises an anti-oxidant.

* * * * *